(12) United States Patent
Lee et al.

(10) Patent No.: US 11,997,767 B2
(45) Date of Patent: May 28, 2024

(54) PULSE SWITCH-BASED POWER SUPPLY SYSTEMS, METHODS, AND DEVICES

(71) Applicant: GOODRICH CORPORATION, Charlotte, NC (US)

(72) Inventors: Yongduk Lee, Vernon, CT (US); Matthew Robert Pearson, Hartford, CT (US)

(73) Assignee: GOODRICH CORPORATION, Charlotte, NC (US)

( * ) Notice: Subject to any disclaimer, the term of this patent is extended or adjusted under 35 U.S.C. 154(b) by 220 days.

(21) Appl. No.: 17/506,518

(22) Filed: Oct. 20, 2021

(65) Prior Publication Data

US 2023/0124043 A1    Apr. 20, 2023

(51) Int. Cl.
*H05B 41/30* (2006.01)
*A61L 2/10* (2006.01)
*A61L 2/12* (2006.01)

(52) U.S. Cl.
CPC .............. *H05B 41/30* (2013.01); *A61L 2/10* (2013.01); *A61L 2202/11* (2013.01); *A61L 2202/14* (2013.01)

(58) Field of Classification Search
CPC ........ H05B 41/30; A61L 2/10; A61L 2202/11; A61L 2202/14
See application file for complete search history.

(56) References Cited

U.S. PATENT DOCUMENTS

| | | | |
|---|---|---|---|
| 5,942,855 A * | 8/1999 | Hopwood | H05H 1/4652 315/111.51 |
| 8,749,154 B2 | 6/2014 | Kitamura et al. | |
| 10,892,141 B2 | 1/2021 | Ziemba et al. | |
| 11,004,660 B2 | 5/2021 | Prager et al. | |
| 11,004,673 B2 | 5/2021 | Park et al. | |
| 2023/0108632 A1 * | 4/2023 | Maa | G02B 5/208 250/454.11 |

FOREIGN PATENT DOCUMENTS

DE    4238388 A1 *    5/1994    .......... B41F 23/0409

OTHER PUBLICATIONS

Power Electronic Pulse Generators for WAter Treatment Application: A Review (Year: 2020).*
European Patent Office, European Search Report dated May 6, 2023 in Application No. 22202016.6.

(Continued)

*Primary Examiner* — Henry Luong
(74) *Attorney, Agent, or Firm* — SNELL & WILMER L.L.P.

(57) ABSTRACT

A sanitization apparatus may include an excimer lamp and a power supply. The power supply includes a power converter including a capacitor, a wide band gap device configured to receive an electric current from the capacitor, and an inductor configured to receive the electric current from the wide band gap device. The power converter is configured to supply a nano second pulse output voltage signal to the excimer lamp.

14 Claims, 8 Drawing Sheets

(56) References Cited

OTHER PUBLICATIONS

Meisser, et al., "Transformerless High Voltage Pulse Generators for Bipolar Drive of Dielectric Barrier Discharges Copper thick-film modules View project Microwave Plasma View project," dated Jan. 31, 2011, Retrieved from the Internet: url: https://www.researchgate.net publication/233386688_Transformerless_High_Voltage_Pulse_Generators_for_Bipolar_Drive_of_Dielectric_Barrier_Di scharges, [retrieved on Feb. 17, 2023].

Jae-Gu Choi, "Introduction of the Magnetic Pulse Compressor (MPC)—Fundamental Review and Practical Application," dated on Sep. 1, 2010, Journal of Electrical Engineering & Technology, [Online] vol. 5, No. 3, 1, pp. 484-492, ISSN: 1975-01-02, DOI: 10.5370/JEET.2010.5.3.484 Retrieved from the Internet: url: http://koreascience.or.kr/article/JAKO201025235525679.pdf>.

Guo et al., "Power Electronic Pulse Generators for Water Treatment Application: A Review," dated Feb. 24, 2020, IEEE Transactions on Power Electronics, Institute of Electrical and Electronics Engineers, USA, vol. 35, No. 10, ISSN: 0885-8993, DOI: 10.1109/TPEL.2976145, pp. 10285-10305, [retrieved on Jun. 29, 2020].

Rueda et al., "Optimum transformer turns ratio for the power supply of dielectric barrier discharge lamps," dated Jan. 12, 2018, IET Power Electronics, IET, UK, vol. 11, No. 1, ISSN:1755-4535, DOI: 10.1049/iet-pel.2016.0497.

* cited by examiner

PULSE SWITCH-BASED POWER SUPPLY SYSTEMS, METHODS, AND DEVICES

FIELD

The present disclosure relates generally to sanitization systems and methods and, more particularly, to power supply systems and methods for ultraviolet (UV) light sanitization systems.

BACKGROUND

The recent novel-coronavirus (SARS-COV-2) outbreak has negatively impacted the safety and health of many people. Pathogens can be transmitted via direct airborne transmission between users or via indirect contact transmission from different users occupying the same space at different times. For example, lingering pathogens may remain on contact surfaces of an aircraft cabin to be spread to passengers and/or crew members on a subsequent flight. The safety of passengers and crew members may be improved by performing disinfecting treatments to surfaces, such as seats, ceiling/wall panels, handles, and lavatory surfaces, etc., to mitigate the presence of pathogens on such surfaces. However, conventional disinfection procedures between flights may take time and may thus adversely affect the operating efficiency of the aircraft (increased interval time between flights), and the effectiveness and quality of such conventional treatments are often difficult to verify/track.

SUMMARY

A sanitization apparatus is disclosed herein, comprising an excimer lamp and a power converter. The power converter comprises a first capacitor, a first wide band gap device configured to receive a first electric current from the first capacitor, and a first inductor configured to receive the first electric current from the first wide band gap device, wherein the power converter is configured to supply an output voltage pulse signal to the excimer lamp.

In various embodiments, the excimer lamp is configured to emit Far-UVC light.

In various embodiments, the first wide band gap device comprises a transistor.

In various embodiments, the first inductor is a variable inductor.

In various embodiments, the sanitization apparatus further comprises a second capacitor, a second wide band gap device configured to receive a second electric current from the second capacitor, and a second inductor.

In various embodiments, the sanitization apparatus further comprises a DC power supply configured to charge the first capacitor when the first wide band gap device is in an OFF state.

In various embodiments, the second capacitor is configured to be charged when the first wide band gap device is in an ON state.

A power converter for an excimer lamp is disclosed. The power converter comprises a first planar capacitor, a first wide band gap device configured to receive a first electric current from the first planar capacitor, and a first planar inductor configured to receive the first electric current from the first wide band gap device.

In various embodiments, the first wide band gap device comprises a transistor selectively switchable between an ON state and an OFF state, wherein in the ON state the first planar inductor is configured to receive the first electric current from the first planar capacitor.

In various embodiments, the power converter further comprises a printed circuit board, wherein the first planar capacitor and the first planar inductor are embedded in the printed circuit board.

In various embodiments, the printed circuit board comprises a first layer comprising the first planar capacitor and a second layer comprising the first planar inductor.

In various embodiments, the printed circuit board further comprises a third layer comprising the first wide band gap device.

In various embodiments, the power converter further comprises a second planar capacitor, a second wide band gap device configured to receive a second electric current from the second planar capacitor, and a second planar inductor configured to receive the second electric current from the second wide band gap device.

In various embodiments, the first inductor comprises a variable inductor.

In various embodiments, the first wide band gap device is coupled in series with the first planar inductor.

In various embodiments, the first wide band gap device comprises a silicon carbide MOSFET.

In various embodiments, the power converter further comprises a printed circuit board, wherein the first wide band gap device, the first planar inductor, and the first planar capacitor are each embedded in the printed circuit board.

A method of powering an excimer lamp is disclosed, comprising charging a first capacitor by a power source, switching a first wide band gap device from an OFF state to an ON state, receiving a first electrical current from the first capacitor by the first wide band gap device, routing the first electrical current to a first inductor by the first wide band gap device, charging a second capacitor with the first electrical current, switching the first wide band gap device from the ON state to the OFF state, switching a second wide band gap device from an OFF state to an ON state, receiving a second electrical current from the second capacitor by the second wide band gap device, routing the second electrical current to a second inductor by the second wide band gap device, and powering the excimer lamp with the second electrical current.

In various embodiments, the first electrical current is received by the first inductor in response to the first wide band gap device switching to the ON state.

In various embodiments, the excimer lamp comprises a Far-UVC light.

The foregoing features and elements may be combined in various combinations without exclusivity, unless expressly indicated herein otherwise. These features and elements as well as the operation of the disclosed embodiments will become more apparent in light of the following description and accompanying drawings.

BRIEF DESCRIPTION OF THE DRAWINGS

The subject matter of the present disclosure is particularly pointed out and distinctly claimed in the concluding portion of the specification. A more complete understanding of the present disclosure, however, may best be obtained by referring to the following detailed description and claims in connection with the following drawings. While the drawings illustrate various embodiments employing the principles described herein, the drawings do not limit the scope of the claims.

DETAILED DESCRIPTION

The following detailed description of various embodiments herein makes reference to the accompanying drawings, which show various embodiments by way of illustration. While these various embodiments are described in sufficient detail to enable those skilled in the art to practice the disclosure, it should be understood that other embodiments may be realized and that changes may be made without departing from the scope of the disclosure. Thus, the detailed description herein is presented for purposes of illustration only and not of limitation. Furthermore, any reference to singular includes plural embodiments, and any reference to more than one component or step may include a singular embodiment or step. Also, any reference to attached, fixed, connected, or the like may include permanent, removable, temporary, partial, full or any other possible attachment option. Additionally, any reference to without contact (or similar phrases) may also include reduced contact or minimal contact. It should also be understood that unless specifically stated otherwise, references to "a," "an" or "the" may include one or more than one and that reference to an item in the singular may also include the item in the plural. Further, all ranges may include upper and lower values and all ranges and ratio limits disclosed herein may be combined.

As used herein, the term "wide band gap" is used to refer to a device having a semiconductor material which has a bandgap in the range of 2-4 electronvolt (eV). Examples of wide band gap semiconductor materials include Silicon Carbide (SiC) and Gallium Nitride (GaN).

In various embodiments, Far-UVC (at or near 222 nm wavelength light) has promise to work in occupied spaces. Excimer lamps utilize a high voltage supply and have a large gas discharge. In various embodiments, the systems and methods disclosed herein are configured to generate nanosecond pulsed power signals for an excimer lamp. Nanosecond pulsed discharge tends to be more homogenous and stable compared with sine AC voltage. Moreover, the plasma gas temperature of the excimer lamp tends to be lower compared with sine AC voltage.

In various embodiments, a power supply as disclosed herein may tend to increase the life of Far-UVC excimer lamps, lower operating temperature, and provide a more stable and homogenous gas discharge.

Figure 1:
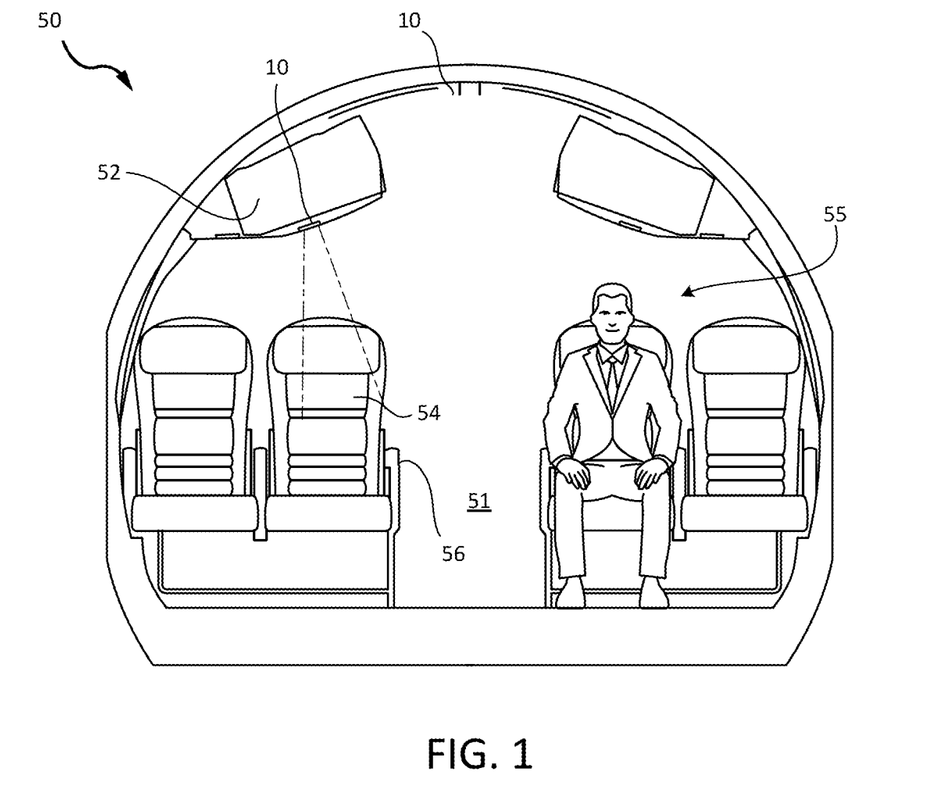
FIG. 1 illustrates a view of a cabin of an aircraft, in accordance with various embodiments.

With reference to FIG. 1, a cabin 51 of an aircraft 50 is shown, according to various embodiments. The aircraft 50 may be any aircraft such as an airplane, a helicopter, or any other aircraft. The aircraft 50 may include various lighting systems 10 that emit visible light to the cabin 51. Pathogens, such as viruses and bacteria, may remain on surfaces of the cabin 51, and these remaining pathogens may result in indirect contact transmission to other people (e.g., subsequent passengers). For example, the cabin 51 may include overhead bins 52, passenger seats 54 for supporting passengers 55, handles 56, lavatory surfaces, and other structures/surfaces upon which active pathogens may temporarily reside. As will be discussed further below, in order to reduce the transmission/transfer of pathogens between passengers, one or more of the lighting systems 10 may blend disinfecting electromagnetic radiation output into the visible light in order to facilitate disinfection of the cabin 51 (e.g., during flights and/or between flights). The lighting systems 10 may be broken down into different addressable lighting regions that could be used on an aircraft. For example, the regions on an aircraft may include sidewall lighting, cross-bin lighting, over wing exit lighting, ceiling lighting, direct lighting, flex lights, reading lights, dome lights, lavatory lights, mirror lights, cockpit lights, cargo lights, etc. The regional breakdown of the lighting system allows lighting control over broad areas of the aircraft. In various embodiments, lighting system 10 may be disposed in/incorporated by a passenger service unit (PSU) for a row of seats. As such, a lighting system 10 could be provided for each row of an aircraft, as well as for each section of different sections of a given row of an aircraft.

Figure 2:
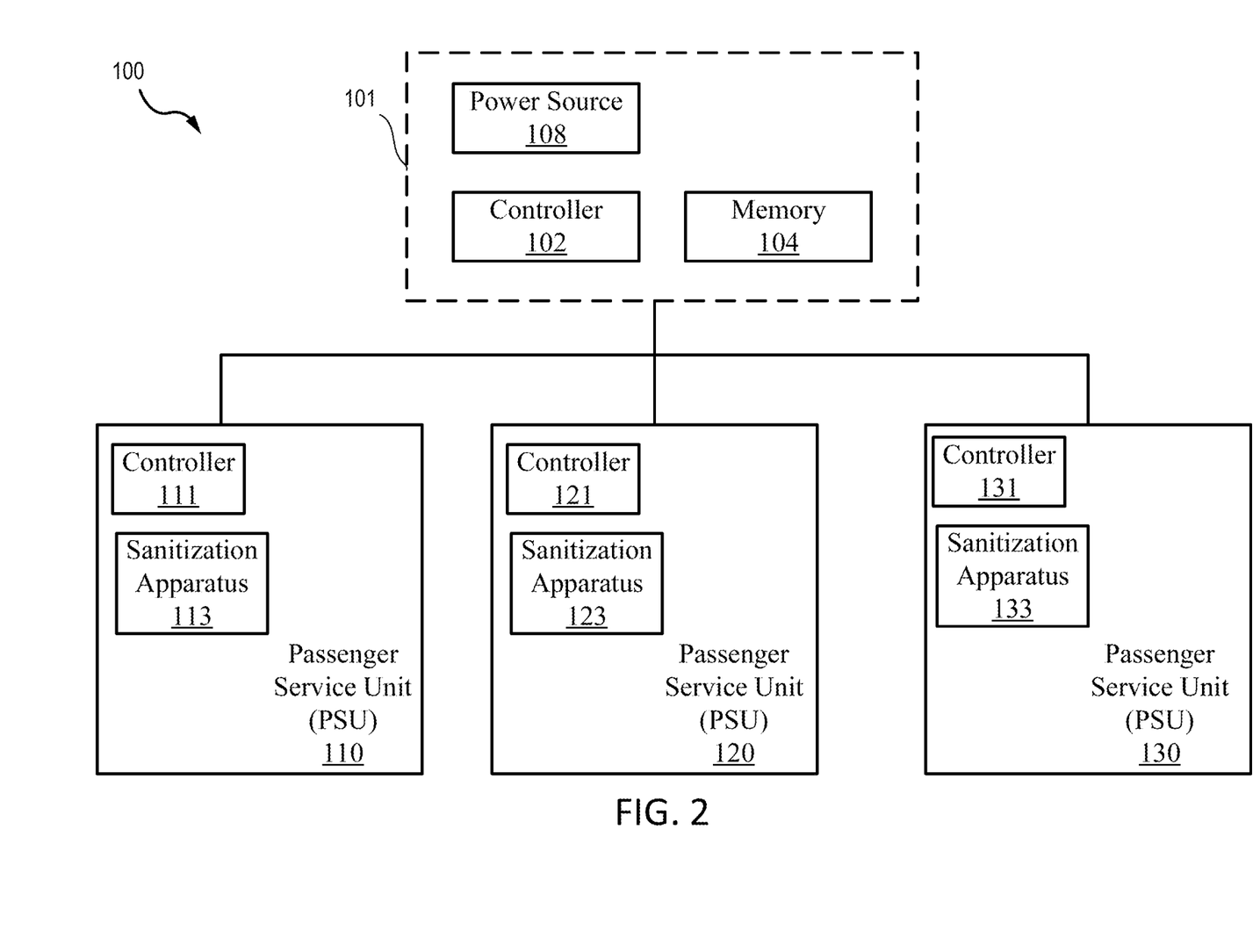
FIG. 2 illustrates a schematic view of a sanitization system, in accordance with various embodiments.

Referring now to FIG. 2 a schematic view of a sanitization system 100 for an aircraft cabin, is illustrated, in accordance with various embodiments. In various embodiments, the sanitization system 100 comprises a main control system 101 and a plurality of PSUs (e.g., first PSU 110, second PSU 120, third PSU 130, etc.). Although illustrated as including three PSUs, the number of PSUs of a sanitization system 100 is not limited in this regard. For example, a PSU may be disposed in each row of seats disposed in a respective column of an aircraft cabin. For example, a cabin with 50 rows and 3 columns may have 150 PSUs (e.g., each row in each column having a PSU). In various embodiments, the PSUs are not limited to rows in the aircraft cabin and may be placed throughout the aircraft cabin as well. For example, PSUs, in accordance with the present disclosure, may be disposed in the lavatory, aisles, cockpit, or any other area of an aircraft cabin where it may be desirable to have sanitization.

In various embodiments, the main control system 101 includes a controller 102 and a memory 104 (e.g., a database or any appropriate data structure; hereafter "memory 104" also may be referred to as "database 104"). The controller 102 may include one or more logic devices such as one or more of a central processing unit (CPU), an accelerated processing unit (APU), a digital signal processor (DSP), a field programmable gate array (FPGA), an application specific integrated circuit (ASIC), or the like (e.g., controller 102 may utilize one or more processors of any appropriate type/configuration, may utilize any appropriate processing architecture, or both). In various embodiments, the controller 102 may further include any non-transitory memory known in the art. The memory 104 may store instructions usable by the logic device to perform operations. Any appropriate computer-readable type/configuration may be utilized as the memory 104. Any appropriate data storage architecture may be utilized by the memory 104.

The database 104 may be integral to the main control system 101 or may be located remote from the main control system 101. The controller 102 may communicate with the database 104 via any wired or wireless protocol. In that regard, the controller 102 may access data stored in the database 104. In various embodiments, the controller 102 may be integrated into computer systems onboard an aircraft. Furthermore, any number of conventional techniques for electronics configuration, signal processing and/or control, data processing and the like may be employed. Also, the processes, functions, and instructions may include software routines in conjunction with processors, etc.

System program instructions and/or controller instructions may be loaded onto a non-transitory, tangible computer-readable medium having instructions stored thereon that, in response to execution by the processor, cause the controller 102 to perform various operations. The term "non-transitory" is to be understood to remove only propagating transitory signals per se from the claim scope and does not relinquish rights to all standard computer-readable media that are not only propagating transitory signals per se. Stated another way, the meaning of the term "non-transitory computer-readable medium" and "non-transitory computer-readable storage medium" should be construed to exclude only those types of transitory computer-readable media which were found in In Re Nuijten to fall outside the scope of patentable subject matter under 35 U.S.C. § 101.

The instructions stored on the memory 104 of the controller 102 may be configured to perform various operations, such as performing cleaning schedules between flights, performing cleaning schedules at predetermined intervals, cleaning a specific row in response to a trigger (i.e., a sneeze or the like), etc.

In various embodiments, the main control system 101 from FIG. 2 further comprises a power source 108. The power source 108 may comprise any power source known in the art, such as a battery, a solar source, a direct current (DC) source, a rechargeable source, or the like.

In various embodiments, the main control system 101 is in operable communication with each PSU in the plurality of PSUs (e.g., PSUs 110, 120, 130). In various embodiments, each PSU comprises a local controller (e.g., controllers 111, 121, 131). Each local controller (e.g., controllers 111, 121, 131) may be in accordance with main controller 102. For example, each local controller (e.g., controllers 111, 121, 131) may include one or more logic devices such as one or more of a central processing unit (CPU), an accelerated processing unit (APU), a digital signal processor (DSP), a field programmable gate array (FPGA), an application specific integrated circuit (ASIC), or the like (e.g., controllers 111, 121, 131 may utilize one or more processors of any appropriate type/configuration, may utilize any appropriate processing architecture, or both). In various embodiments, the controllers 111, 121, 131 may each further include any non-transitory memory that is known in the art. The memory may store instructions usable by the logic device to perform operations. Any appropriate computer-readable type/configuration may be utilized as the memory. Any appropriate data storage architecture may be utilized by the memory.

In various embodiments, each PSU (e.g., PSUs 110, 120, 130) may comprise a sanitization apparatus (e.g., sanitization apparatus 113, 123, 133). As described further herein, the controller 102 may command the various local controllers (e.g., controllers 111, 121, 131) to instruct the devices therein. In various embodiments, the power source 108 is sized and configured to power all of the sanitization apparatus (e.g., sanitization apparatus 113, 123, 133) of all of the PSUs (e.g., PSUs 110, 120, 130, etc.) of sanitization system 100.

In various embodiments, each sanitization apparatus (e.g., sanitization apparatus 113, 123, 133) may be connected via digital communications, discrete communications, or wireless communications to a respective local controller (e.g., controllers 111, 121, 131).

In various embodiments, the sanitization apparatus 113 may comprise a Far-UVC light source. Sanitization apparatus 113 may comprise an excimer lamp. In various embodiments, any light source capable of outputting a light with a wavelength of about 222 nm is within the scope of this disclosure. Sanitization apparatus 113 may be configured to generate a Far-UVC light having a wavelength of between 200 and 230 nm, in accordance with various embodiments. Sanitization apparatus 113 may be configured to generate a Far-UVC light having a wavelength of between 200 and 225 nm, in accordance with various embodiments. Sanitization apparatus 113 may be configured to generate a Far-UVC light having a wavelength of between 207 and 225 nm, in accordance with various embodiments. Sanitization apparatus 113 may be configured to generate a Far-UVC light having a wavelength of about 222 nm, wherein the term "about" in this regard can only refer to a wavelength of 222 nm±15 nm. In various embodiments, the sanitization apparatus 113 is in operable communication with local controller 111 and/or a main controller 102. In this regard, in response to receiving a signal from a controller (e.g., local controller 111 and/or a main controller 102), the light source may be activated and generate Far-UVC disinfecting light.

Figure 3:
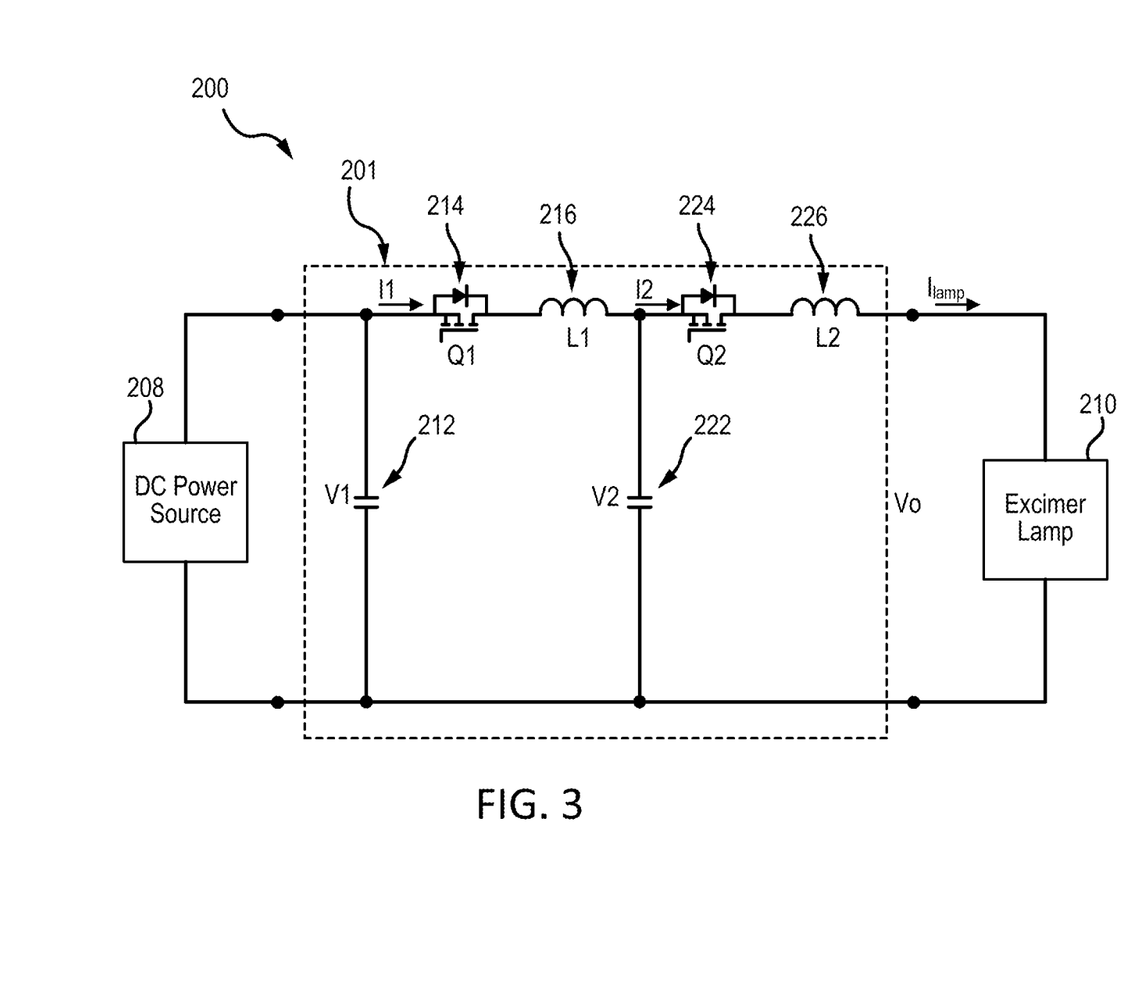
FIG. 3 illustrates a schematic view of a sanitization apparatus connected with a power source, in accordance with various embodiments.

With reference to FIG. 3, a schematic view of a sanitization apparatus 200 connected with a power source 208 is illustrated, in accordance with various embodiments. In various embodiments, sanitization apparatus 200 is similar to sanitization apparatus 113 of FIG. 2. Sanitization apparatus 200 includes an excimer lamp 210. Sanitization apparatus 200 includes a power converter 201 (also referred to herein as a pulse-switch based power converter) for supplying power to excimer lamp 210. Power converter 201 may receive an input DC power signal from power source 208. Power converter 201 may receive an input DC power signal from power source 208 comprising a 28 volt DC power signal, though other voltage levels are contemplated herein, such as 12V DC and 48V DC.

The power supply (i.e., power source 208 and power converter 201) is configured to supply nanosecond pulse output voltage power signals for powering excimer lamp 210. Power converter 201 includes a capacitor 212 (also referred to herein as a first capacitor), a wide band gap (WBG) device 214 (also referred to herein as a first WBG device), and an inductor 216 (also referred to herein as a first inductor. Capacitor 212, WBG device 214, and inductor 216 may form one compressor stage. In the illustrated embodiment, power converter 201 includes a second compressor stage comprising a capacitor 222 (also referred to herein as a second capacitor), a wide band gap (WBG) device 224 (also referred to herein as a second WBG device), and an inductor 226 (also referred to herein as a second inductor. However, it is contemplated herein that power converter 201 may comprise only a single compressor stage (see FIG. 5) or may comprise more than two compressor stages (see FIG. 6).

In various embodiments, the topology of power converter 201 may allow to achieve a desired output voltage shape for excimer lamp 210 without the use of a transformer.

In various embodiments, WBG device 214 comprises a transistor selectively switchable between an ON state and an OFF state (e.g., by controller 102 and/or controller 111 of FIG. 2). In various embodiments, WBG device 214 comprises a Silicon Carbide (SiC) metal-oxide-semiconductor field-effect transistor (MOSFET). WBG device 214 may comprise a single SiC MOSFET. In various embodiments, WBG device 214 comprises a plurality of Gallium Nitride (GaN) MOSFETS arranged in series. Inductor 216 may be coupled in series with WBG device 214. With WBG device 214 in the ON state, the inductor 216 is configured to receive electric current I1 from capacitor 212 and/or power source 208. Stated differently, in response to WBG device 214 being switched to the ON state, capacitor 212 may discharge, causing the inductor 216 to receive electric current I1 at least in part from capacitor 212. With WBG device 214 in the OFF state, the inductor 216 is electrically disconnected from capacitor 212 and/or power source 208. With WBG device 214 in the OFF state, capacitor 212 may be charged by DC power source 208.

In various embodiments, WBG device 224 similarly comprises a transistor selectively switchable between an ON state and an OFF state (e.g., by controller 102 and/or controller 111 of FIG. 2). In various embodiments, WBG device 224 comprises a Silicon Carbide (SiC) MOSFET. WBG device 224 may comprise a single SiC MOSFET. In various embodiments, WBG device 224 comprises a plurality of Gallium Nitride (GaN) MOSFETS arranged in series. With WBG device 224 in the ON state, the inductor 226 is configured to receive electric current I2 from capacitor 222 and/or inductor 216. Stated differently, in response to WBG device 224 being switched to the ON state, capacitor 222 may discharge, causing the inductor 226 to receive electric current I2 at least in part from capacitor 222. With WBG device 224 in the OFF state, the inductor 226 is electrically disconnected from capacitor 222 and/or inductor 216. With WBG device 224 in the OFF state, capacitor 222 may be charged by inductor 216.

WBG device 214 and WBG device 224 may be selectively switched between their ON and OFF states to generate a nanosecond pulse output voltage Vo.

Figure 5:
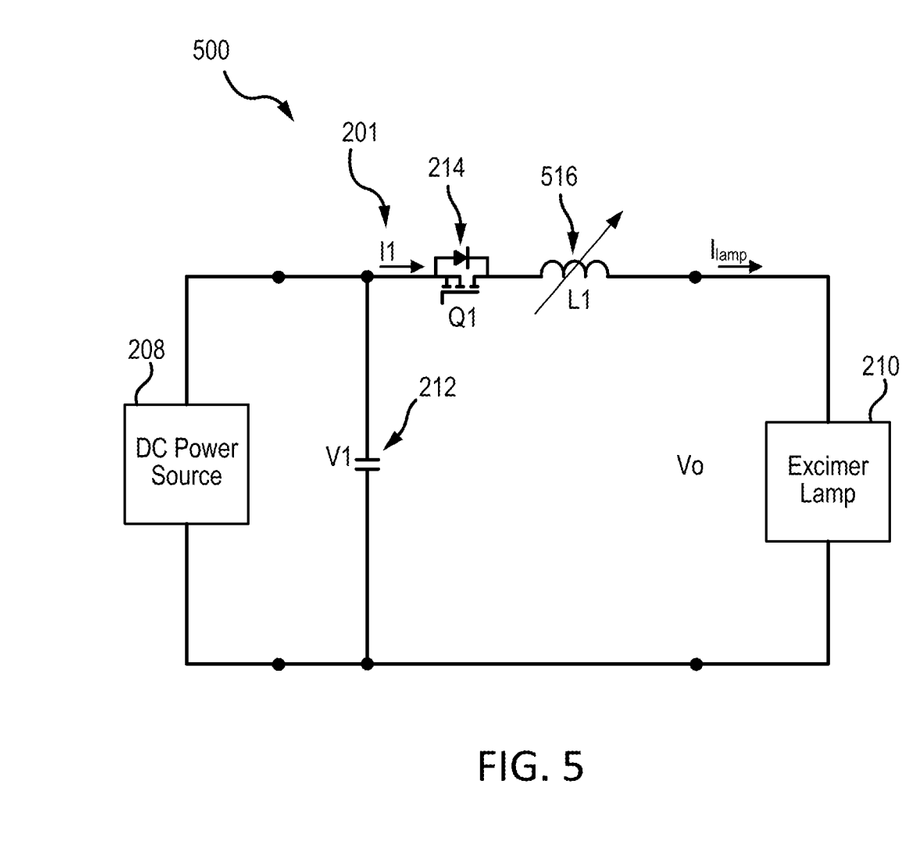
FIG. 5 illustrates a circuit diagram of a sanitization apparatus power converter comprising a single compressor stage, in accordance with various embodiments.

With reference to FIG. 5, various electric currents and voltages of power converter 201 are illustrated during operation of power of sanitization apparatus 200. Voltage signal 402 represents the voltage V1 across capacitor 212. In various embodiments, the peak voltage of voltage signal 402 (i.e., the maximum voltage V1 across capacitor 212) may be less than 3,000 volts (<3 kV).

Figure 4:
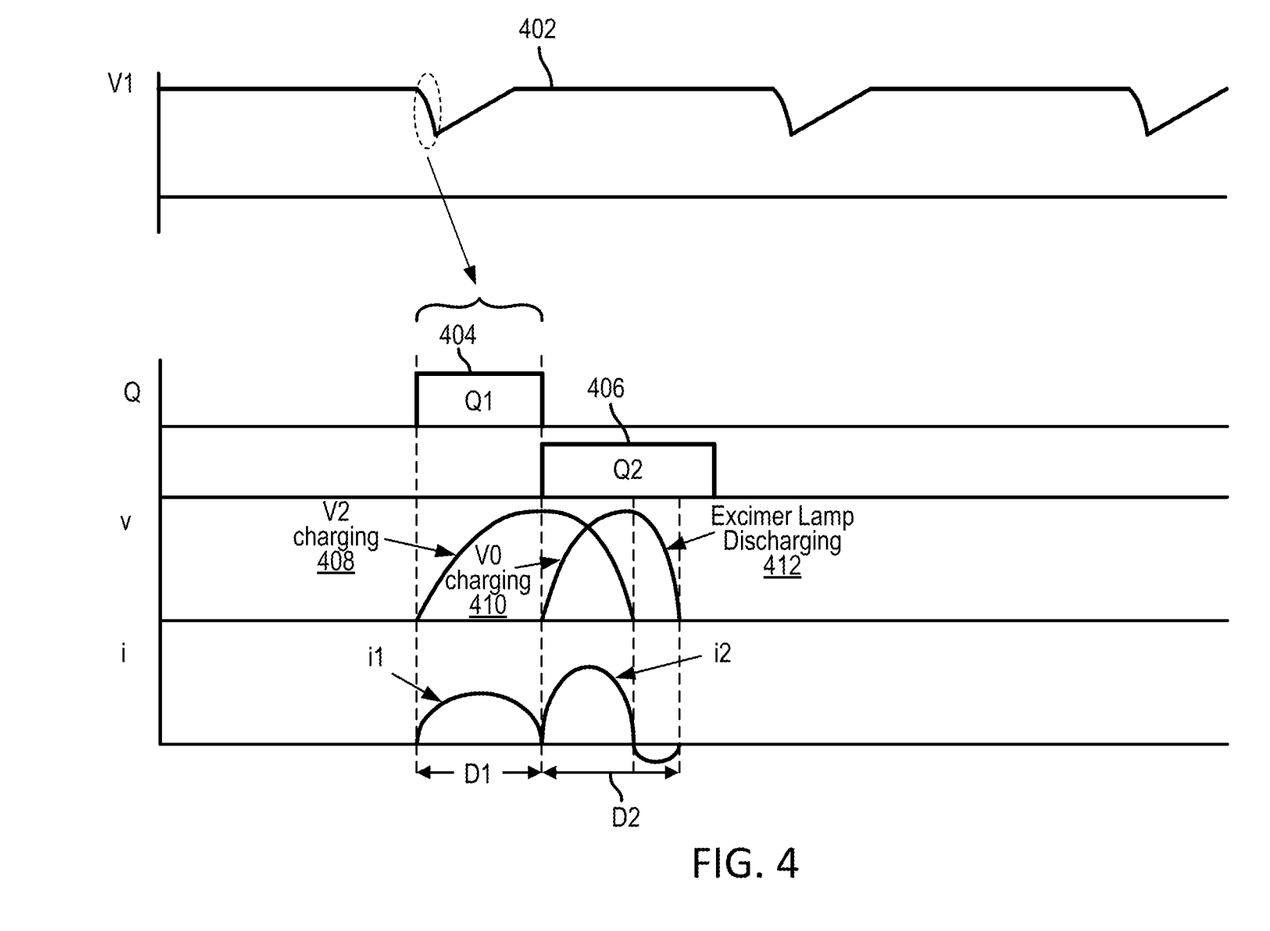
FIG. 4 illustrates a plot of electric signals of the sanitization apparatus of FIG. 3 during operation of the sanitization apparatus, in accordance with various embodiments.

With combined reference to FIG. 3 and FIG. 4, WBG device 214 may be switched from an OFF state to an ON state (see signal 404). WBG device 224 may be in an OFF state when WBG device 214 is switched to the ON state. In response to WBG device 214 being switched to the ON state, inductor 216 begins to charge. In response to WBG device 214 being switched to the ON state, capacitor 222 voltage V2 begins to charge (see signal 408). As capacitor 222 is charged, current i1 flows through WBG device 214 until capacitor 212 is fully charged. WBG device 214 may be in the ON state for a duration D1.

Next, WBG device 214 may be switched from the ON state to the OFF state (see signal 404) and WBG device 214 may be switched from an OFF state to an ON state (see signal 406). In various embodiments, WBG device 214 may be switched from the ON state to the OFF state (see signal 404) and WBG device 214 may be simultaneously switched from the OFF state to the ON state (see signal 406). In response to WBG device 224 being switched to the ON state, capacitor 222 voltage V2 begins to discharge (see signal 408) into inductor 226 and the inductor 226 begins to charge. In response, output voltage Vo may sharply increase in a pulse-like manner (see signal 410) and the output voltage is supplied to excimer lamp 210. In response, the excimer lamp 210 may generate a plasma discharge between its electrodes, thereby emitting an ultraviolet light, as the excimer lamp discharges (see signal 412). As capacitor 222 is discharged, current i2 flows through WBG device 224 until excimer lamp 210 is fully discharged. In this manner, power converter 201 generates a pulse switch-based output voltage. Each output voltage pulse (see signal 410, 412) may comprise a duration D2 of about one nanosecond. WBG device 224 may be in the ON state for at least a duration D2 to ensure that excimer lamp 210 utilizes the energy stored in capacitor 222.

The above process (i.e., the sequential switching ON and OFF of WBG devices 214, 224) may be repeated for a desired duration for nanosecond pulsed discharge of excimer lamp 210. In various embodiments, power converter 201 is configured to provide an output voltage Vo having a peak voltage of about 3,000 volts (3 kV). In this manner, power converter 201 generate an output voltage pulse signal having a maximum voltage greater than that of the input DC voltage.

With reference to FIG. 5, a sanitization apparatus 500 having a single compressor stage is illustrated, in accordance with various embodiments. Sanitization apparatus 500 may be similar to sanitization apparatus 200 of FIG. 3, except that sanitization apparatus 500 comprises a topology comprising only a single compressor stage. With respect to FIG. 5, elements with like element numbering, as depicted in FIG. 3, are intended to be the same and will not necessarily be repeated for the sake of clarity. Sanitization apparatus 500 may include an inductor 516. Inductor 516 may be similar to inductor 216, except that inductor 516 may be a variable inductor. In this manner, the LC resonant frequency of circuit 501 may be controlled.

Figure 6:
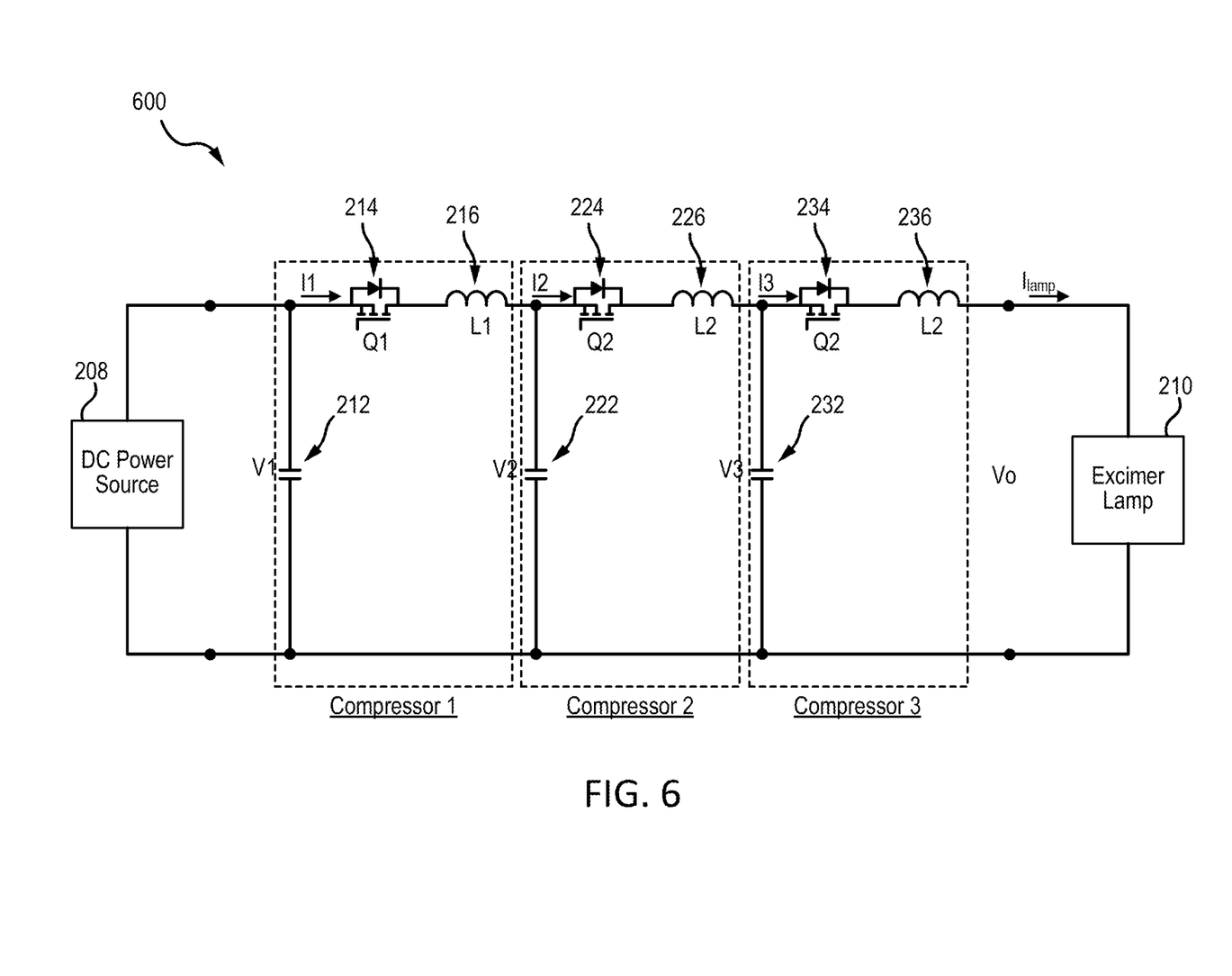
FIG. 6 illustrates a circuit diagram of a sanitization apparatus comprising three compressor stages, in accordance with various embodiments.

With reference to FIG. 6, a sanitization apparatus 600 having a plurality of compressor stages is illustrated, in accordance with various embodiments. Sanitization apparatus 600 may be similar to sanitization apparatus 200 of FIG. 3, except that sanitization apparatus 600 comprises a topology comprising three compressor stages. With respect to FIG. 6, elements with like element numbering, as depicted in FIG. 3, are intended to be the same and will not necessarily be repeated for the sake of clarity. Sanitization apparatus 600 may include a third capacitor 232, a third WBG device 234, and a third inductor 236. Providing sanitization apparatus 600 with more compressor stages may provide an output voltage Vo with a nanosecond pulse having a sharper shape (i.e., having a greater slope).

Figure 7:
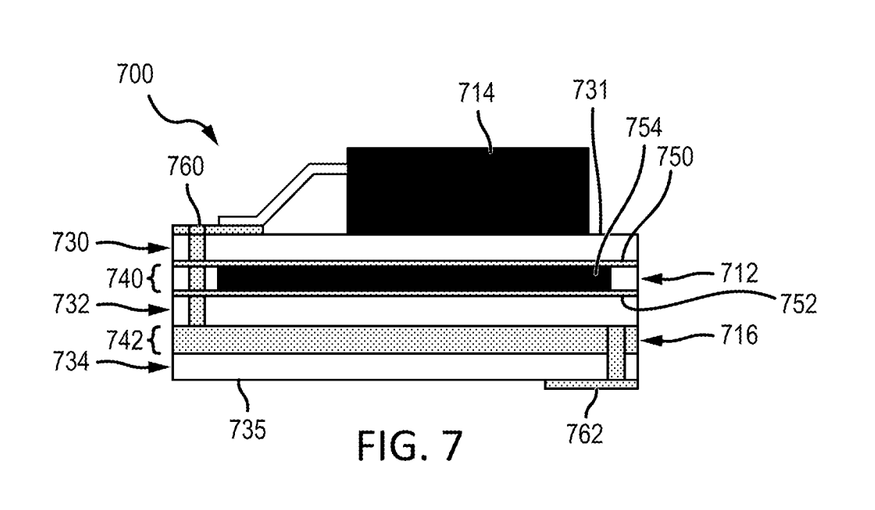
FIG. 7 illustrates a schematic view of a power converter circuit for a sanitization apparatus, the power converter circuit having an embedded planar capacitor and an embedded planar inductor, in accordance with various embodiments.

With reference to FIG. 7, a printed circuit board (PCB) 700 is illustrated, in accordance with various embodiments. In various embodiments, power converter 201 of FIG. 3 may comprise PCB 700. PCB 700 may comprise a planar capacitor 712. In various embodiments, capacitor 212 of FIG. 3 is similar to planar capacitor 712. PCB 700 may comprise a first layer 740 comprising planar capacitor 712. Planar capacitor 712 may be embedded in PCB 700. PCB 700 may include a top layer 730 defining a first external surface 731 of PCB 700. Planar capacitor 712 may be located internally from top layer 730.

Planar capacitor 712 may comprise a first planar electrode 750, a second planar electrode 752, and an insulator 754 (e.g., a dielectric material) disposed between the first electrode 750 and the second electrode 752.

PCB 700 may further comprise a planar inductor 716. In various embodiments, inductor 216 of FIG. 3 is similar to planar inductor 716. PCB 700 may comprise a second layer 742 comprising planar inductor 716. Planar inductor 716 may be embedded in PCB 700. PCB 700 may include an internal layer 732 located between planar capacitor 712 and planar inductor 716. PCB 700 may include an bottom layer 734 defining a second external surface 735. Planar inductor 716 may be located internally from bottom layer 734. Planar inductor 716 may be located between bottom layer 734 and internal layer 732.

PCB 700 may further comprise a WBG device 714. WBG device 714 may be disposed at external surface 731. An electrical contact 760 may be disposed at external surface 731. Electrical contact 760 may comprise a conductive material, such as copper for example. An electrical contact 762 may be disposed at second external surface 735. Electrical contact 762 may comprise a conductive material, such as copper for example. WBG device may be electrically coupled to electrical contact 760. Electrical contact 760 may be electrically coupled with electrical contact 762 via planar capacitor 712 and planar inductor 716.

Top layer 730, internal layer 732, and bottom layer 734 may each comprise a non-conductive substrate. In this regard, top layer 730, internal layer 732, and bottom layer 734 may be electrically insulating layers.

Figure 8:
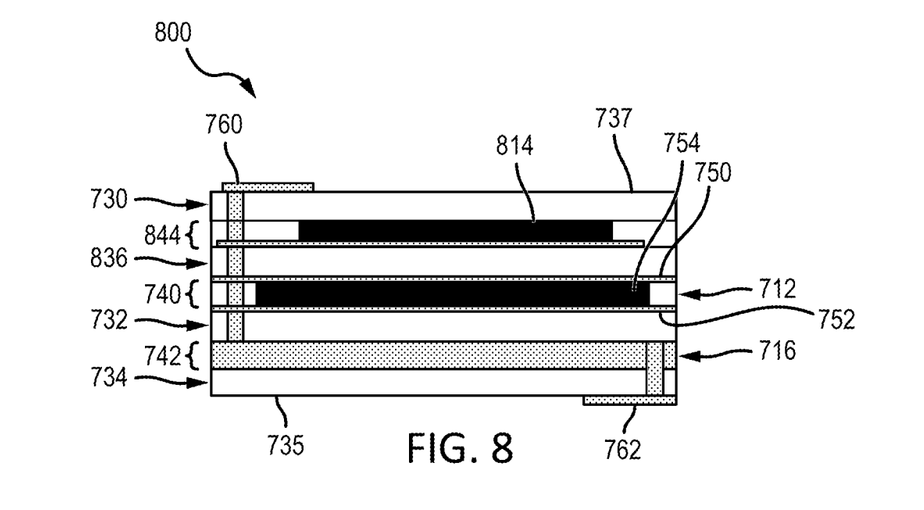
FIG. 8 illustrates a schematic view of a power converter circuit for a sanitization apparatus, the power converter circuit having an embedded wide band gap device, an embedded planar capacitor, and an embedded planar inductor, in accordance with various embodiments.

With reference to FIG. 8, a PCB 800 is illustrated, in accordance with various embodiments. PCB 800 may be similar to PCB 700 of FIG. 7, except that PCB 800 comprises an embedded WBG device 814. With respect to FIG. 8, elements with like element numbering, as depicted in FIG. 7, are intended to be the same and will not necessarily be repeated for the sake of clarity. In various embodiments, power converter 201 of FIG. 3 may comprise PCB 800. PCB 800 may comprise embedded WBG device 814. In various embodiments, WBG device 214 of FIG. 3 is similar to WBG device 814. PCB 800 may comprise a third layer 844 comprising WBG device 814. WBG device 814 may be located internally from top layer 730.

PCB 800 may include an internal layer 836 located between WBG device 814 and planar capacitor 712. Internal layer 836 may comprise a non-conductive substrate. In this regard, internal layer 836 may be an electrically insulating layer.

Figure 9:
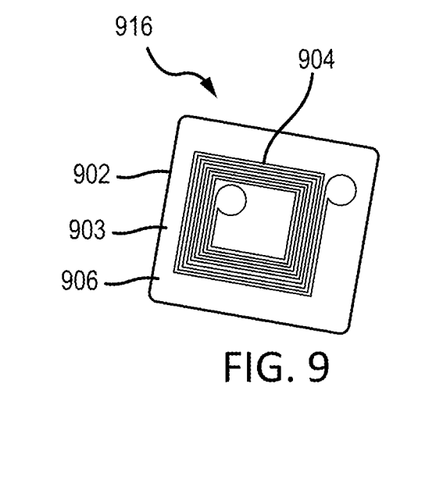
FIG. 9 illustrates a perspective view of a planar inductor, in accordance with various embodiments.

With reference to FIG. 9, a planar inductor 916 is illustrated, in accordance with various embodiments. Planar inductor 916 may comprise a planar body 902 comprising an electrically insulating material 903 and a plurality of windings 904 arranged on a planar surface 906 of the planar body 902.

Figure 10:
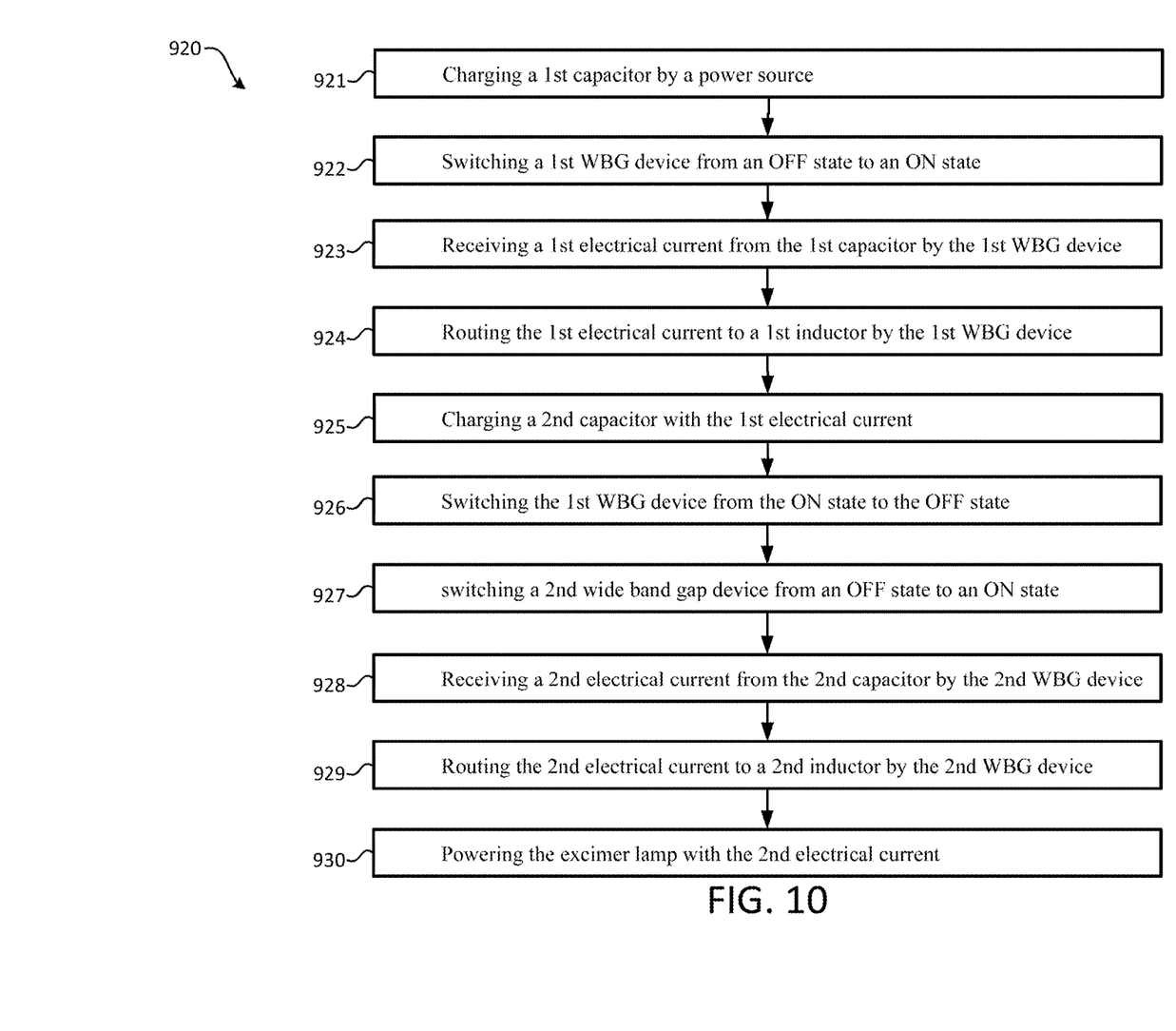
FIG. 10 is a process for powering a sanitization apparatus, in accordance with various embodiments.

With reference to FIG. 10, a method 920 is illustrated. Method 920 may be a method of powering an excimer lamp. Method 920 includes charging a first capacitor by a power source (step 921). Method 920 includes switching a first wide band gap device from an OFF state to an ON state (step 922). Method 920 includes receiving a first electrical current from the first capacitor by the first wide band gap device (step 923). Method 920 includes routing the first electrical current to a first inductor by the first wide band gap device (step 924). Method 920 includes charging a second capacitor with the first electrical current (step 925). Method 920 includes switching the first wide band gap device from the ON state to the OFF state (step 926). Method 920 includes switching a second wide band gap device from an OFF state to an ON state (step 927). Method 920 includes receiving a second electrical current from the second capacitor by the second wide band gap device (step 928). Method 920 includes routing the second electrical current to a second inductor by the second wide band gap device (step 929). Method 920 includes powering the excimer lamp with the second electrical current (step 930).

With combined reference to FIG. 3 and FIG. 10, step 921 may include charging capacitor 212 by power source 208. Step 922 may include switching WBG device 214 from an OFF state to an ON state (see signal 404 of FIG. 4). Step 923 may include receiving a first electrical current I1 at least in part from capacitor 212 by WBG device 214. Step 924 may include routing the first electrical current I1 to inductor 216 by WBG device 214. Step 925 may include charging capacitor 222 with the first electrical current I1 in response to WBG device 214 switching from the OFF state to the ON state. Step 926 may include switching the WBG device 214 from the ON state to the OFF state (see signal 404 of FIG. 4). Step 927 may include switching WBG device 224 from an OFF state to an ON state (see signal 406 of FIG. 4). Step 928 may include receiving a second electrical current I2 at least in part from capacitor 222 by WBG device 224. Step 929 may include routing the second electrical current I2 to inductor 226 by WBG device 224. Step 930 may include powering the excimer lamp 210 with the second electrical current I2 (and associated voltage waveform Vo).

Benefits, other advantages, and solutions to problems have been described herein with regard to specific embodiments. Furthermore, the connecting lines shown in the various figures contained herein are intended to represent exemplary functional relationships and/or physical couplings between the various elements. It should be noted that many alternative or additional functional relationships or physical connections may be present in a practical system. However, the benefits, advantages, solutions to problems, and any elements that may cause any benefit, advantage, or solution to occur or become more pronounced are not to be construed as critical, required, or essential features or elements of the disclosure. The scope of the disclosure is accordingly to be limited by nothing other than the appended claims, in which reference to an element in the singular is not intended to mean "one and only one" unless explicitly so stated, but rather "one or more." Moreover, where a phrase similar to "at least one of A, B, or C" is used in the claims, it is intended that the phrase be interpreted to mean that A alone may be present in an embodiment, B alone may be present in an embodiment, C alone may be present in an embodiment, or that any combination of the elements A, B and C may be present in a single embodiment; for example, A and B, A and C, B and C, or A and B and C. Different cross-hatching is used throughout the figures to denote different parts but not necessarily to denote the same or different materials.

Systems, methods and apparatus are provided herein. In the detailed description herein, references to "one embodiment," "an embodiment," "various embodiments," etc., indicate that the embodiment described may include a particular feature, structure, or characteristic, but every embodiment may not necessarily include the particular feature, structure, or characteristic. Moreover, such phrases are not necessarily referring to the same embodiment. Further, when a particular feature, structure, or characteristic is described in connection with an embodiment, it is submitted that it is within the knowledge of one skilled in the art to affect such feature, structure, or characteristic in connection with other embodiments whether or not explicitly described. After reading the description, it will be apparent to one skilled in the relevant art(s) how to implement the disclosure in alternative embodiments.

Furthermore, no element, component, or method step in the present disclosure is intended to be dedicated to the public regardless of whether the element, component, or method step is explicitly recited in the claims. No claim element herein is intended to invoke 35 U.S.C. 112(f) unless the element is expressly recited using the phrase "means for." As used herein, the terms "comprises," "comprising," or any other variation thereof, are intended to cover a non-exclusive inclusion, such that a process, method, article, or apparatus that comprises a list of elements does not include only those elements but may include other elements not expressly listed or inherent to such process, method, article, or apparatus.

Finally, it should be understood that any of the above described concepts can be used alone or in combination with any or all of the other above described concepts. Although various embodiments have been disclosed and described, one of ordinary skill in this art would recognize that certain modifications would come within the scope of this disclosure. Accordingly, the description is not intended to be exhaustive or to limit the principles described or illustrated herein to any precise form. Many modifications and variations are possible in light of the above teaching.

What is claimed is:

1. A sanitization apparatus comprising:
   an excimer lamp configured to emit Far-UVC light; and
   a power converter comprising:
      a first capacitor;
      a first wide band gap device comprising a transistor and configured to receive a first electric current from the first capacitor; and
      a first inductor configured to receive the first electric current from the first wide band gap device, wherein the first inductor is a variable inductor;
   wherein the power converter is configured to supply an output voltage pulse signal to the excimer lamp.

2. The sanitization apparatus of claim 1, further comprising:
   a second capacitor;
   a second wide band gap device configured to receive a second electric current from the second capacitor; and
   a second inductor.

3. The sanitization apparatus of claim 2, wherein the second capacitor is configured to be charged when the first wide band gap device is in an ON state.

4. The sanitization apparatus of claim 1, further comprising a DC power supply configured to charge the first capacitor when the first wide band gap device is in an OFF state.

5. A power converter for an excimer lamp comprising:
   a first planar capacitor;
   a first wide band gap device configured to receive a first electric current from the first planar capacitor;
   a first planar inductor configured to receive the first electric current from the first wide band gap device, wherein the first wide band gap device comprises a transistor selectively switchable between an ON state and an OFF state, wherein in the ON state the first planar inductor is configured to receive the first electric current from the first planar capacitor; and
   a printed circuit board comprising a first layer and a second layer wherein the first planar capacitor is embedded in the first layer of the printed circuit board and the first planar inductor is embedded in the second layer of the printed circuit board.

6. The power converter of claim 5, wherein the printed circuit board further comprises a third layer comprising the first wide band gap device.

7. The power converter of claim 5, further comprising:
   a second planar capacitor;
   a second wide band gap device configured to receive a second electric current from the second planar capacitor; and
   a second planar inductor configured to receive the second electric current from the second wide band gap device.

8. The power converter of claim 5, wherein the first planar inductor comprises a variable inductor.

9. The power converter of claim 5, wherein the first wide band gap device is coupled in series with the first planar inductor.

10. The power converter of claim 5, wherein the first wide band gap device comprises a silicon carbide MOSFET.

11. The power converter of claim 5, further comprising a printed circuit board, wherein the first wide band gap device, the first planar inductor, and the first planar capacitor are each embedded in the printed circuit board.

12. A method of powering an excimer lamp, comprising:
   charging a first capacitor by a power source;
   switching a first wide band gap device from an OFF state to an ON state;
   receiving a first electrical current from the first capacitor by the first wide band gap device;
   routing the first electrical current to a first inductor by the first wide band gap device;
   charging a second capacitor with the first electrical current;
   switching the first wide band gap device from the ON state to the OFF state;
   switching a second wide band gap device from an OFF state to an ON state;
   receiving a second electrical current from the second capacitor by the second wide band gap device;
   routing the second electrical current to a second inductor by the second wide band gap device; and
   powering the excimer lamp with the second electrical current.

13. The method of claim 12, wherein the first electrical current is received by the first inductor in response to the first wide band gap device switching to the ON state.

14. The method of claim 13, wherein the excimer lamp comprises a Far-UVC light.

* * * * *